(12) United States Patent
Kawahara et al.

(10) Patent No.: US 10,006,066 B2
(45) Date of Patent: Jun. 26, 2018

(54) MODIFIED CYANOBACTERIA

(71) Applicants: Kao Corporation, Chuo-ku, Tokyo (JP); Saitama University, Saitama-shi, Saitama (JP)

(72) Inventors: Akihito Kawahara, Wakayama (JP); Yukako Sonoike, Saitama (JP)

(73) Assignees: Kao Corporation, Tokyo (JP); Saitama University, Saitama-shi, Saitama (JP)

(*) Notice: Subject to any disclaimer, the term of this patent is extended or adjusted under 35 U.S.C. 154(b) by 0 days. days.

(21) Appl. No.: 15/111,692

(22) PCT Filed: Jan. 30, 2015

(86) PCT No.: PCT/JP2015/052618
§ 371 (c)(1),
(2) Date: Jul. 14, 2016

(87) PCT Pub. No.: WO2015/115583
PCT Pub. Date: Aug. 6, 2015

(65) Prior Publication Data
US 2017/0159084 A1 Jun. 8, 2017

(30) Foreign Application Priority Data
Jan. 31, 2014 (JP) .................. 2014-016524

(51) Int. Cl.
| | | |
|---|---|---|
| C12P 7/64 | (2006.01) |
| C07K 14/195 | (2006.01) |
| C12N 9/10 | (2006.01) |
| C12N 9/16 | (2006.01) |
| C07K 14/405 | (2006.01) |
| C12N 9/00 | (2006.01) |

(52) U.S. Cl.
CPC .......... *C12P 7/6409* (2013.01); *C07K 14/195* (2013.01); *C07K 14/405* (2013.01); *C12N 9/1029* (2013.01); *C12N 9/16* (2013.01); *C12N 9/93* (2013.01); *C12Y 301/02014* (2013.01); *C12Y 602/0102* (2013.01); *C12Y 203/01041* (2013.01)

(58) Field of Classification Search
None
See application file for complete search history.

(56) References Cited

U.S. PATENT DOCUMENTS

| | | | | |
|---|---|---|---|---|
| 8,835,137 | B2 * | 9/2014 | Roberts .................... | C12N 1/20 435/134 |
| 2009/0298143 | A1 | 12/2009 | Roessler et al. | |
| 2012/0237987 | A1 * | 9/2012 | Curtiss, III .............. | C12N 1/20 435/134 |

FOREIGN PATENT DOCUMENTS

| | | |
|---|---|---|
| JP | 2011-505838 A | 3/2011 |
| JP | 2011-229482 A | 11/2011 |
| JP | 2014-014334 A | 1/2014 |
| WO | WO 2009/076559 | 6/2009 |

OTHER PUBLICATIONS

Hanai et al., The Effects of Dark Incubation on Cellular Metabolism of the Wild Type *Cyanobacterium synechocystis* sp. PCC 6803 and a Mutant Lacking the Transcriptional Regulator cyAbrB2, Life, 2014, 4, 770-87.*
International Search Report (ISR) for PCT/JP2015/052618; I.A. fd Jan. 30, 2015, dated Apr. 28, 2015, by the Japan Patent Office, Tokyo, Japan.
International Preliminary Report on Patentability (IPRP), Chapter I of the Patent Cooperation Treaty, including the Written Opinion for PCT/JP2015/052618; I.A. fd Jan. 30, 2015, dated Aug. 2, 2016, by the International Bureau of WIPO, Geneva, Switzerland.
Yamauchi, Y. et al., "Physiological roles of the cyAbrB transcriptional regulator pair SII0822 and SII0359 in *Synechocystis* sp. strain PCC 6803," J Bacteriol. Aug. 2011;193(15):3702-9. doi: 10.1128/JB.00284-11. Epub Jun. 3, 2011, American Society for Microbiology, Washington, DC.
Kaniya, Y. et al., "Deletion of the transcriptional regulator cyAbrB2 deregulates primary carbon metabolism in *Synechocystis* sp. PCC 6803," Plant Physiol. Jun. 2013;162(2):1153-63. doi: 10.1104/pp.113.218784. Epub Apr. 15, 2013, American Society of Plant Biologists, Rockville, MD.
Database DDBJ/EMBL/GenBank [online] Accession No. ELR87398, www.ncbi.nih.gov/protein/ELR87398.1?report=genpept, uploaded Jan. 17, 2013 [retrieved on Apr. 16, 2015] Shih, P.M. et al., Definition: AMP-forming long-chain acyl-CoA synthetase [*Synechocystis* sp. PCC 7509].
Kaczmarzyk, D et al., "Fatty acid activation in cyanobacteria mediated by acyl-acyl carrier protein synthetase enables fatty acid recycling," Plant Physiol. Mar. 2010;152(3):1598-610. doi: 10.1104/pp.109.148007. Epub Jan. 8, 2010, American Society of Plant Biologists, Rockville, MD.
Yoshino, F. et al., "High photobiological hydrogen production activity of a *Nostoc* sp. PCC 7422 uptake hydrogenase-deficient mutant with high nitrogenase activity," Mar Biotechnol (NY). Jan.-Feb. 2007;9(1):101-12. Epub Nov. 28, 2006, Springer-Verlag New York Inc.
Deng, M-D et al., "Ethanol synthesis by genetic engineering in cyanobacteria," Appl Environ Microbiol. Feb. 1999;65(2):523-528, American Society for Microbiology, Washington, DC.
Atsumi, S et al., "Direct photosynthetic recycling of carbon dioxide to isobutyraldehyde," Nat Biotechnol. Dec. 2009;27(12):1177-80. doi: 10.1038/nbt.1586, Nature America Publishing, New York, NY.

(Continued)

*Primary Examiner* — Tekchand Saidha
*Assistant Examiner* — Todd M Epstein
(74) *Attorney, Agent, or Firm* — Sterne, Kessler, Goldstein & Fox P.L.L.C.

(57) ABSTRACT

Provided is a cyanobacterium with improved productivity of fatty acid. A method for producing a modified cyanobacterium, comprising causing loss of functions of an AbrB-like transcriptional regulator and acyl-ACP synthetase in a cyanobacterium.

26 Claims, 5 Drawing Sheets

(56) References Cited

OTHER PUBLICATIONS

Liu, X et al., "Fatty acid production in genetically modified cyanobacteria," Proc Natl Acad Sci U S A. Apr. 26, 2011;108(17):6899-904.doi: 10.1073/pnas.1103014108. Epub Apr. 11, 2011, National Academy of Sciences, Washington, DC.

Ishii, A et al., An AbrB-like transcriptional regulator, SII0822, is essential for the activation of nitrogen-regulated genes in *Synechocystis* sp. PCC 6803, Plant Physiol. Sep. 2008;148(1):660-70. doi: 10.1104/pp.108.123505. Epub Jul. 30, 2008, American Society of Plant Biologists, Rockville, MD.

Lieman-Hurwitz, J et al., "A cyanobacterial AbrB-like protein affects the apparent photosynthetic affinity for $CO_2$ by modulating low-$CO_2$-induced gene expression," Environ Microbiol. Apr. 2009;11(4):927-36. doi: 10.1111/j.1462-2920.2008.01818.x. Epub Dec. 10, 2008, Blackwell Science, Oxford, England.

\* cited by examiner

[Fig.1]
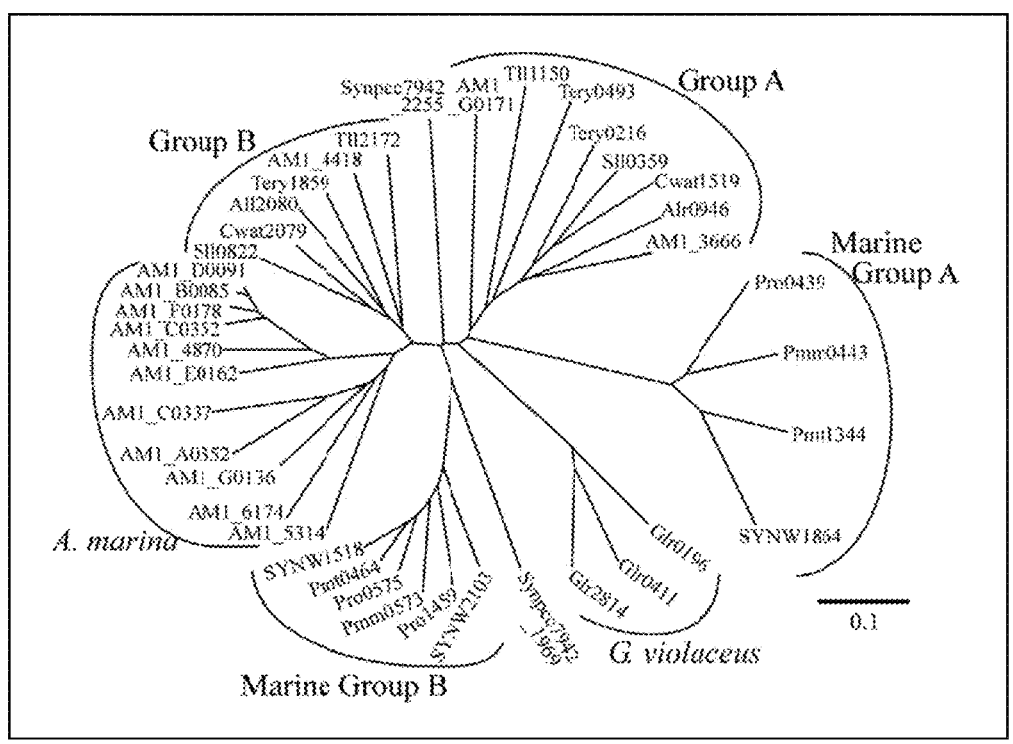

[Fig.2]
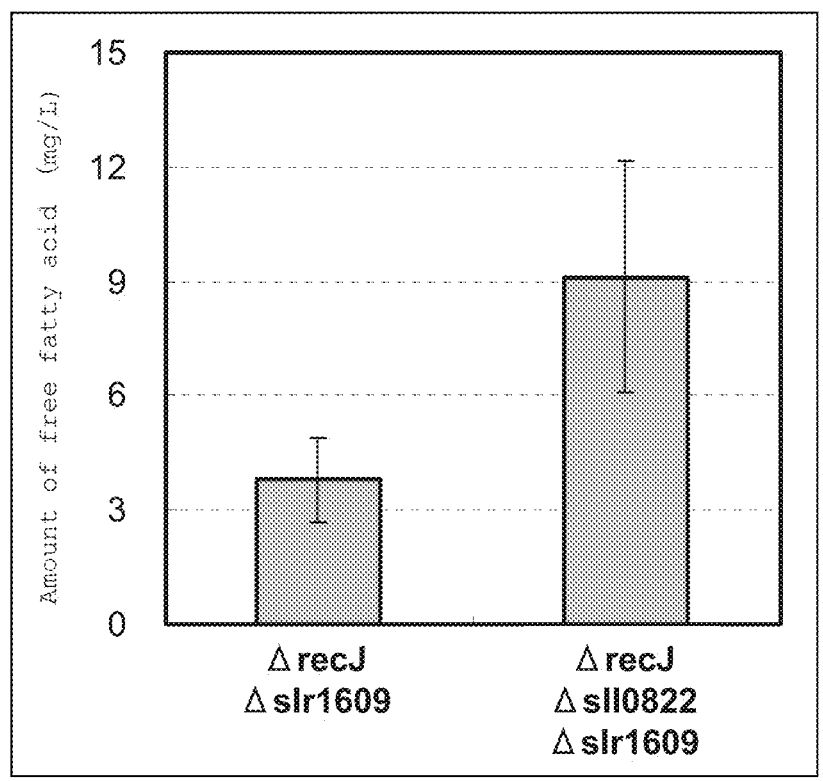

[Fig.3]
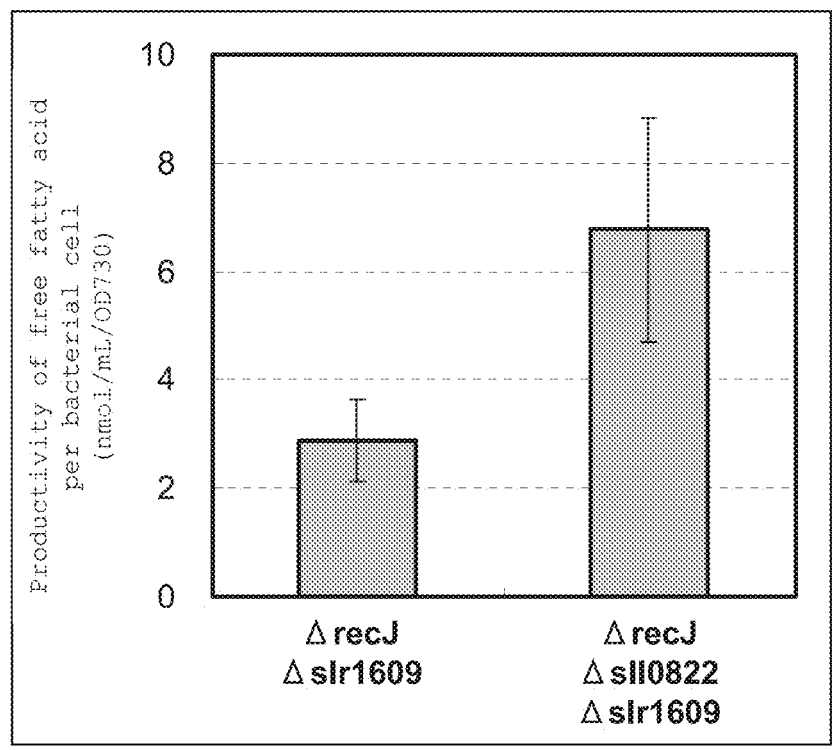

[Fig.4]
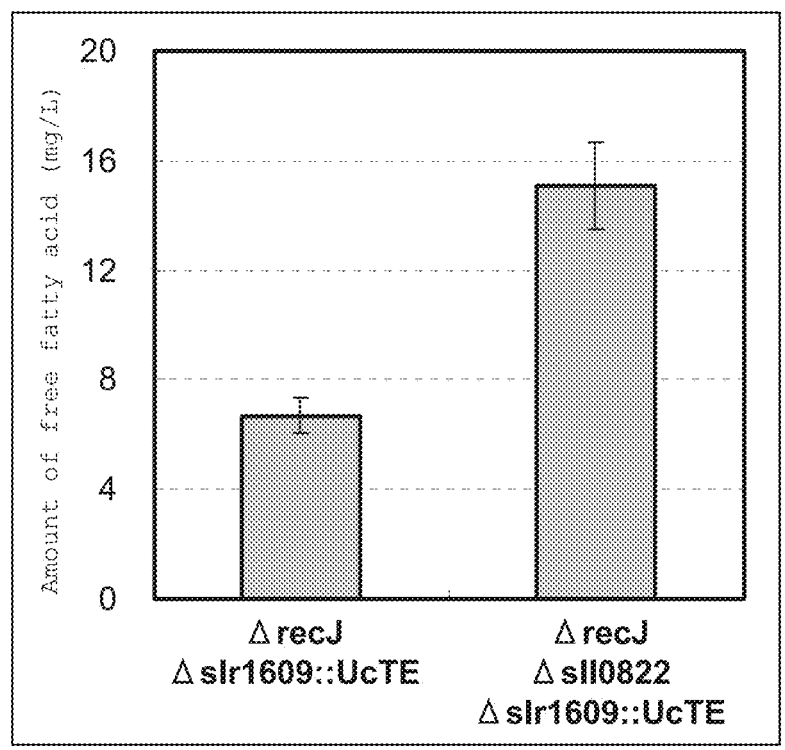

[Fig.5]
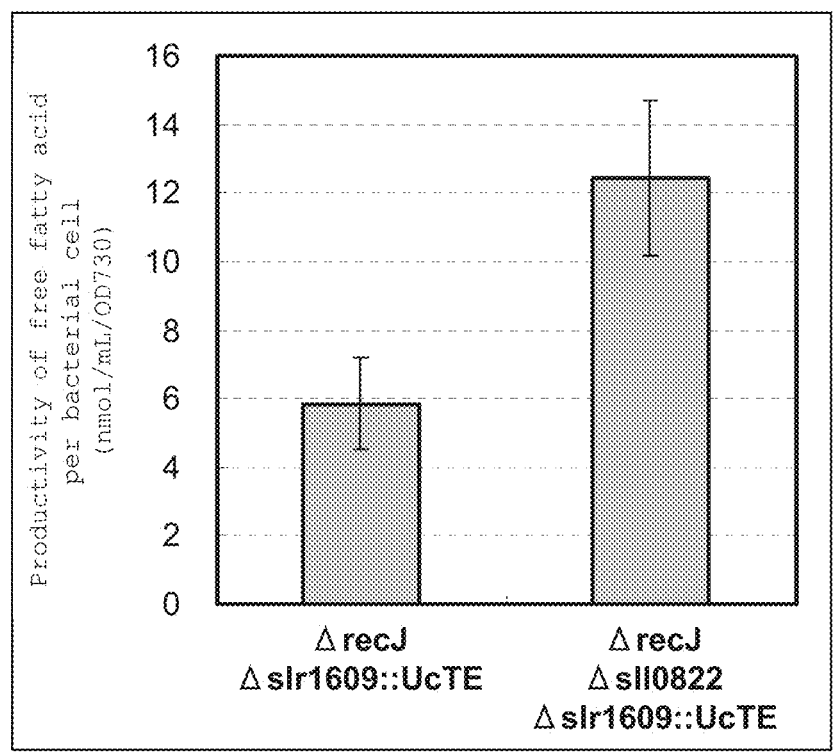

MODIFIED CYANOBACTERIA

REFERENCE TO SEQUENCE LISTING SUBMITTED ELECTRONICALLY

The content of the electronically submitted substitute sequence listing, file name 2537_1240001_Sequence_Listing.txt, size 14,882 bytes; and date of creation Aug. 8, 2017, filed herewith, is incorporated herein by reference in its entirety.

FIELD OF THE INVENTION

The present invention relates to modified cyanobacteria improved in fatty acid secretory productivity.

BACKGROUND OF THE INVENTION

Recently, it has been predicted that fossil fuels would be depleted in future. In order to solve energy problems, it is an urgent need to establish technologies for producing next-generation energy alterative to fossil fuels. As one of them, a technology for biofuel production using photosynthetic organisms such as cyanobacteria and algae has attracted attention and been researched. The photosynthetic organisms can produce biofuels from carbon, which was photosynthetically fixed from $CO_2$ and water by using light as an energy source. In addition, the photosynthetic organisms are not competitive with food raw materials and can realize carbon-neutral fuel production. Because of these advantages, the photosynthetic organisms are expected as a next-generation energy production system.

Cyanobacteria (also known as blue-green algae) belong to a group of eubacteria and have an ability to fix $CO_2$ and produce oxygen through photosynthesis. Cyanobacteria, which have an outer membrane and a cell wall formed of peptidoglycan, fall into the category of gram-negative bacteria but are phylogenetically far from typical gram-negative bacteria. More than billion years ago, cyanobacteria were engulfed by eukaryotic cells. Such intracellular symbiont (primary symbiosis), cyanobacteria, are considered as an origin of chloroplasts. Thus cyanobacteria have been widely used in photosynthesis studies as an ancestor organism of chloroplasts.

Cyanobacteria grow fast, have a high photosynthetic ability, and have a transformation ability. Because of this, cyanobacterial cells, to which foreign DNA is introduced, can be used in microbiological production of substances and thus have attracted attention as a microbial host for producing a biofuel. As examples of biofuels produced by cyanobacteria, hydrogen (Non-Patent Literature 1), ethanol (Non-Patent Literature 2), isobutanol (Non-Patent Literature 3) and fatty acids (Non-Patent Literature 4) have been reported. Non-Patent Literature 4 and Patent Literature 1 describe a method for converting inorganic carbon to a fatty acid by culturing a recombinant cyanobacterial cell producing exogenic acyl-ACP thioesterase. Patent Literature 2 describes that the amount of carbon assimilation per cell volume is increased by inducing functional loss of a gene for an AbrB-like transcriptional regulator (cyAbrB) in a cyanobacterium.

Meanwhile, Non-Patent Literature 5 reports that an AbrB-like transcriptional regulator, Sll0822, of *Synechocystis* sp. PCC6803, is essential for activating transcription of a gene involved in nitrogen metabolism, and that, the expression levels of genes involved in fatty acid biosynthesis became equal to or lower than those of a wild-type strain in a strain having a deletion of gene sll0822. Non-Patent Literature 6 suggests that Sll0822 serves as a repressor of a gene involved in an inorganic carbon uptake system in high $CO_2$ conditions, and presumably serves as a factor involved in regulating C/N balance in cells.

(Patent Literature 1) JP-A-2011-505838

(Patent Literature 2) JP-A-2011-229482

(Non-Patent Literature 1) Yoshino F. et al. (2007) Mar. Biotechnol. 9: 101-112

(Non-Patent Literature 2) Deng M. D. and Coleman J. R. (1999) Appl. Environ Microbiol. 65: 523-528

(Non-Patent Literature 3) Atsumi S. et al. (2009) Nat. Biotechnol. 27: 1177-1180

(Non-Patent Literature 4) Liu X. et al. (2011) Proc. Natl. Acad. Sci. USA. 108: 6899-6904

(Non-Patent Literature 5) Ishii A. and Hihara Y. (2008) Plant Physiol. 148: 660-670

(Non-Patent Literature 6) Lieman-Hurwitz J. et al. (2009) Environ Microbiol. 11: 927-936

SUMMARY OF THE INVENTION

In an aspect, the present invention provides a method for producing a modified cyanobacterium, comprising causing loss of functions of an AbrB-like transcriptional regulator and acyl-ACP synthetase in a cyanobacterium.

In another aspect, the present invention provides a modified cyanobacterium losing functions of an AbrB-like transcriptional regulator and acyl-ACP synthetase.

In a further aspect, the present invention provides a modified cyanobacterium as mentioned above and a method for producing a fatty acid, comprising culturing the aforementioned modified cyanobacterium produced by the aforementioned method.

In a still further aspect, the present invention provides a method for improving fatty acid secretory productivity of a cyanobacterium, comprising causing loss of functions of an AbrB-like transcriptional regulator and acyl-ACP synthetase in the cyanobacterium.

BRIEF DESCRIPTION OF THE DRAWINGS

FIG. 1 shows an unrooted phylogenetic tree of cyanobacterial AbrB-like transcriptional regulators (cyAbrB). The unrooted phylogenetic tree was prepared based on the amino acid sequences of putative transcriptional regulators having an AbrB DNA binding domain at the C-terminal side, in 12 types of cyanobacteria in accordance with the neighbor-joining method using CLUSTALW program ver1.83.

FIG. 2 is a graph showing the amount of free fatty acid in a broth of each of in ΔrecJΔslr1609::sp strain and ΔrecJΔsll0822Δslr1609::sp strain (n=3, error bar=SD).

FIG. 3 is a graph showing free fatty acid productivity per cell of each of ΔrecJΔslr1609::sp strain and ΔrecJΔsll0822Δslr1609::sp strain (n=3, error bar=SD).

FIG. 4 is a graph showing the amount of free fatty acid in a broth of each of ΔrecJΔslr1609::UcTE strain and ΔrecJΔsll0822Δslr1609::UcTE strain (n=3, error bar=SD).

FIG. 5 is a graph showing free fatty acid productivity per cell of ΔrecJΔslr1609::UcTE strain and ΔrecJΔsll0822Δslr1609::UcTE strain (n=3, error bar=SD).

DETAILED DESCRIPTION OF THE INVENTION (1. Definition)

In the specification, nucleotide sequence identity and amino acid sequence identity are calculated in accordance with the Lipman-Pearson method (Science, 1985, 227: 1435-1441). More specifically, they were calculated by analysis using genetic information processing software, Genetyx-Win homology (Search homology) analysis program, assuming that the unit size to compare (ktup) is specified to 2.

In the specification, the concept of "loss" of function includes partial loss of function (that is, reduction, suppression or partial inhibition of function) and complete loss of function. For example, in the specification, the "functional loss of an AbrB-like transcriptional regulator" may mean that the function of the regulator decreases or is completely lost. In the specification, the "functional loss of acyl-ACP synthetase" may mean that the acyl-ACP synthetic activity of the enzyme decreases or is substantially completely lost. For example, "functional loss of an AbrB-like transcriptional regulator or acyl-ACP synthetase in a cyanobacterium" may refer to lowering the expression level of the regulator or the enzyme, thereby decreasing AbrB transcriptional regulatory function or acyl-ACP synthetic activity in a cyanobacterium; or refer to deleting a gene encoding the regulator or the enzyme.

Cyanobacteria, which is also known as blue-green algae, belong to a group of prokaryotes carrying out photosynthesis using chlorophyll. Cyanobacteria are highly diversified. In view of cell morphology, there are bacteria having a unicellular shape, such as *Synechocystis* sp. PCC6803, bacteria having a filamentous shape formed of many cells connected like a string, such as nitrogen fixing bacteria, *Anabaena* sp. PCC7120 forming heterocysts, and bacteria having a spiral shape and a branched shape. In view of growth environment, there are a wide variety of bacteria adapted in various conditions including thermophilic bacteria such as *ThermoSynechococcus elongatus* BP-1 isolated from Beppu Onsen; and oceanic bacteria such as *Synechococcus* sp. CC9311 living in the coast or *Synechococcus* sp. WH8102 living in the outer sea. As bacteria having feature intrinsic to the species, *Microcystis aeruginosa*, which has gas vacuoles and can produce toxin; *Gloeobacter violaceus* PCC7421 having no thylakoid and a light harvesting antenna, i.e., phycobilisome, bound to plasma membrane; and oceanic *Acaryochloris marina* having chlorophyll d as a main (>95%) photosynthetic pigment in place of chlorophyll a, as is in general photosynthetic organisms, are mentioned.

The AbrB-like transcriptional regulator is a protein having an AbrB DNA binding domain, widely distributed in gram-positive bacteria, gram-negative bacteria and archaea and known to serve as a transcription factor playing an important role in regulating gene expression. For example, it is reported in *bacillus subtilis* that the AbrB-like transcriptional regulator is involved in e.g., sporulation, competence or nutrient source acquisition in the transition period from a logarithmic growth phase to a stationary phase. Most AbrB-like transcriptional regulators have a DNA binding domain at their N-terminal sides; but the AbrB-like transcriptional regulators derived from cyanobacteria exceptionally have a DNA binding domain at the C-terminal sides. A gene encoding such an AbrB-like transcriptional regulator has been conserved in all cyanobacteria whose entire genomic nucleotide sequences are opened to public; but the gene is never seen in other bacterial groups (Non-Patent Literature 5). Because of this, the AbrB-like transcriptional regulator having a DNA binding domain at the C-terminal side is sometimes referred to as cyAbrB in the sense that the AbrB-like transcriptional regulator is intrinsic to cyanobacteria (Patent Literature 2). Also in the specification, the AbrB-like transcriptional regulator of cyanobacteria is sometimes referred to as "cyAbrB" or "cyAbrB family".

When the number of genes encoding cyAbrB was investigated with respect to cyanobacteria whose genomic nucleotide sequences are open to public, many species have two copies or more genes. It was found that *Synechococcus* sp. CC9902 has four copies and *Synechococcus* sp. CC9605 has five copies. It should be noted that *Acaryochloris marina*, whose entire genomic sequence has recently been elucidated, has, in total, 14 copies in the genome and the plasmid. The cyAbrBs are classified into several groups based on their structural similarity. Multiple copies present in the genome of the same cyanobacterium phylogenetically often belong to different groups. For example, two copies present in e.g., *Synechocystis* sp. PCC6803, *Crocosphaera watsonii* WH8501, *Anabaena* sp. PCC7120, *Trichodesmium erythraeum* IMS101 and *ThermoSynechococcus elongatus* BP-1 belong to group A and group B, respectively; whereas two copies present in oceanic *Synechococcus* and *Prochlorococcus* form Marine group A and B, respectively, which are different from the above groups A and B. Furthermore, the cyAbrBs in *Acaryochloris marina* and *Gloeobacter violaceus* individually form their own groups.

FIG. 1 shows an unrooted phylogenetic tree of cyAbrB derived from 12 types of cyanobacteria in accordance with the neighbor-joining method using CLUSTALW program ver1.83. In FIG. 1, the names of organisms and names of cyAbrB are expressed by abbreviation; for example, Sll0822 represents *Synechocystis* sp. PCC6803 strain, Sll0822 (gi16331736). Information on types of cyanobacteria having cyAbrB and cyAbrB which individual cyanobacteria have shown in FIG. 1 can be obtained from, for example, the CyanoBase ([genome.microbedb.jp/cyanobase/]) or the NCBI database ([www.ncbi.nlm.nih.gov/genome/] or [www.ncbi.nlm.nih.gov/protein/]).

In cyanobacteria, carbon dioxide fixed by photosynthesis is converted into acetyl-CoA via a large number of enzymatic reaction processes. In the initial stage of fatty acid synthesis, malonyl-CoA is synthesized from acetyl-CoA and $CO_2$ by the function of acetyl-CoA carboxylase. Next, malonyl-CoA is converted into malonyl-ACP by the function of malonyl CoA:ACP transacylase. Thereafter, while fatty acid synthetase (or acyl-ACP synthetase) progressively works, two carbon units are sequentially added to synthesize acyl-ACP, which are increased in two carbons and used as an intermediate for synthesizing e.g., a membrane lipid.

Information on genes and proteins of cyanobacteria is open to public, for example, in the aforementioned CyanoBase and the NCBI database. Those skilled in the art can obtain the amino acid sequence of a desired protein (for example, cyAbrB or acyl-ACP synthetase) of a cyanobacterium or the nucleotide sequences of a gene encoding of the protein based on information of these database.

(2. Modified Cyanobacterium)

Various techniques for producing biofuels from carbon (raw material) of atmospheric $CO_2$ depending upon cyanobacterium photosynthesis have been developed; however, their productivity is still low. In the context, development of a technique for more efficiently producing biofuel has been desired. The present invention relates to providing cyanobacteria with improved productivity of fatty acid.

The present inventors prepared a modified cyanobacterium by causing loss of functions of both AbrB-like transcriptional regulator and acyl-ACP synthetase in a cyanobacterium or by further introducing a gene encoding acyl-ACP thioesterase in the cyanobacterium. As a result, they found that the quantity of fatty acid secretory production per broth of the cyanobacterium or bacterial cell increases.

The present invention enables obtaining a modified cyanobacterium improved in fatty acid secretory productivity. If the modified cyanobacterium of the present invention is cultured, microbiological fatty acid can be efficiently produced.

The present invention provides a modified cyanobacterium with improved secretory productivity of fatty acid. The modified cyanobacterium of the present invention is a cyanobacterium modified by causing loss of the functions of an AbrB-like transcriptional regulator (cyAbrB) and acyl-ACP synthetase.

The type of cyanobacterium (hereinafter sometimes referred to as a parent cyanobacterium) serving as a parent microorganism of the modified cyanobacterium of the present invention, in other words, the type of cyanobacterium before losing functions of cyAbrB and acyl-ACP synthetase is not particularly limited and any type of cyanobacterium can be used. Examples of the parent cyanobacterium are preferably cyanobacteria belonging to *Synechocystis, Synechococcus, Thermosynechococcus, Trichodesmium, Acaryochloris, Crocosphaera* and *Anabaena*; more preferably, cyanobacteria belonging to *Synechocystis, Synechococcus, ThermoSynechococcus* or *Anabaena*; more preferably, *Synechocystis* sp. PCC6803, *Synechocystis* sp. PCC7509, *Synechocystis* sp. PCC6714, *Synechococcus* sp. PCC7942, *ThermoSynechococcus elongatus* BP-1, *Trichodesmium erythraeum* IMS101, *Acaryochloris mariana* MBIC11017, *Crocosphaera watsonii* WH8501 and *Anabaena* sp. PCC7120; and further preferably, *Synechocystis* sp. PCC6803, *Synechocystis* sp. PCC6714 and *Synechocystis* sp. PCC7509; and still further preferably *Synechocystis* sp. PCC6803.

The amino acid sequence of cyAbrB of a parent cyanobacterium, a gene encoding the amino acid sequence, the position of the gene on the genome or a plasmid, and the nucleotide sequence of the gene can be checked on the aforementioned CyanoBase and NCBI database. As shown in FIG. 1, cyAbrBs are categorized into several groups phylogenetically different from each other and multiple cyAbrBs belonging to different lineage groups are sometimes conserved in a single cyanobacterium species. Alternatively, cyAbrB is sometimes encoded by a gene present not only on the genome of a cyanobacterium but also on a plasmid. The cyAbrB, the function of which is to be lost in the present invention, is not limited as long as it is conserved in a parent cyanobacterium and it is not limited by its phylogenetical group or the site (on the genome or plasmid) where the gene is present.

For example, as the cyAbrB, the function of which is to be lost in the present invention, those shown in FIG. 1 are mentioned. Examples of the cyAbrB, the function of which is to be lost; if *Synechocystis* is a parent cyanobacterium, include Sll0359, Sll0822, Syn7509DRAFT_00022930, Syn7509DRAFT_00034400 and Syn7509DRAFT_00025140; if *Synechococcus* is a parent cyanobacterium, include SYNPCC7002_A0129, SYNPCC7002_A1095, Synpcc7942_1969, Synpcc7942_2255, Syc1843_c and Syc2126_c; if *ThermoSynechococcus* is a parent cyanobacterium, include Tll2172 and Tll1150; if *Trichodesmium* is a parent cyanobacterium, include Tery0216, Tery0493 and Tery1859; if *Acaryochloris* is a parent cyanobacterium, include AM1_3666, AM1_4418 and AM1_5314; if *Crocosphaera* is a parent cyanobacterium, include Cwat1519 and Cwat2079; and if *Anabaena* is a parent cyanobacterium, include Alr0946, All2080, Ava_0524 and Ava_3125. As the cyAbrB, the function of which is to be lost in the present invention, preferably cyAbrB belonging to group B of the cyAbrB family is mentioned. Specific examples thereof include Sll0822 of *Synechocystis* sp. PCC6803, Syn7509DRAFT_00022930 of *Synechocystis* sp. PCC7509, Synpcc7942_2255 of *Synechococcus* sp. PCC7942, Tll2172 of *ThermoSynechococcus elongatus* BP-1, Tery1859 of *Trichodesmium erythraeum* IMS101, AM1_4418 of *Acaryochloris mariana* MBIC11017, Cwat2079 of *Crocosphaera watsonii* WH8501 and All2080 of *Anabaena* sp. PCC7120. Alternatively, as the cyAbrB, the function of which is to be lost in the present invention, a polypeptide having the amino acid sequence having an identity of 40% or more with any one of the amino acid sequences of cyAbrB proteins mentioned above, preferably 50% or more, more preferably 60% or more, further preferably 70% or more, still further preferably 80% or more, still further preferably 90% or more, still further preferably 95% or more, still further preferably 98% or more and still further preferably 99% or more; and having an AbrB transcriptional regulatory function, can be mentioned.

The amino acid sequence of the acyl-ACP synthetase of a cyanobacterium and a gene encoding the amino acid sequence, the position of the gene and the nucleotide sequence thereof can be checked on the aforementioned CyanoBase and NCBI database. In the present invention, preferable examples of the acyl-ACP synthetase, the function of which is to be lost from a parent cyanobacterium, include Slr1609 of *Synechocystis* sp. PCC6803, Syn7509DRAFT_00010940 of *Synechocystis* sp. PCC7509, Synpcc7942_0918 of *Synechococcus* sp. PCC7942, Tll1301 of *ThermoSynechococcus elongates* BP-1, Tery_1829 of *Trichodesmium erythraeum* IMS101, AM1_5562 and AM1_2147 of *Acaryochloris mariana* MBIC11017, Cwat_5663 of *Crocosphaera watsonii* WH8501 and Alr3602 of *Anabaena* sp. PCC7120. Alternatively, the acyl-ACP synthetase, the function of which is to be lost in the present invention, a polypeptide having the amino acid sequence having an identity of 40% or more with any one of the amino acid sequences of acyl-ACP synthetase proteins mentioned above, preferably 50% or more, more preferably 60% or more, further preferably 70% or more, further more preferably 80% or more, still further preferably 90% or more, still further preferably 95% or more, still further preferably 98% or more and still further preferably 99% or more, and having a function of synthesizing acyl-ACP, can be mentioned.

As means for causing loss of the function of an AbrB-like transcriptional regulator (cyAbrB) or acyl-ACP synthetase in cyanobacteria is not particularly limited as long as it is usually used in causing loss of function of proteins. For example, deleting or inactivating a gene encoding cyAbrB or acyl-ACP synthetase; introducing a mutation that inhibits transcription of the gene; inhibiting translation of a transcript of the gene; or administering an inhibitor specifically inhibiting a desired protein expressed is mentioned. In the present invention, in order to cause loss of the functions of an AbrB-like transcriptional regulator (cyAbrB) and acyl-ACP synthetase in a cyanobacterium, it is more preferable to delete or inactivate a gene encoding an AbrB-like transcriptional regulator (cyAbrB) and a gene encoding acyl-ACP synthetase in the cyanobacterium.

In the present invention, as an example of the gene encoding cyAbrB to be deleted or inactivated in order to cause loss of the function of cyAbrB, a gene belonging to group B of the cyAbrB family is preferable; and a polynucleotide encoding cyAbrB as shown in FIG. 1 and a polynucleotide encoding Sll0822 of *Synechocystis* sp. PCC6803, Syn7509DRAFT_00022930 of *Synechocystis* sp. PCC7509, Synpcc7942_2255 of *Synechococcus* sp. PCC7942, Tll2172 of *ThermoSynechococcus elongatus* BP-1, Tery1859 of *Trichodesmium erythraeum* IMS101, AM1_4418 of *Acaryochloris mariana* MBIC11017, Cwat2079 of *Crocosphaera watsonii* WH8501 or All2080 of *Anabaena* sp. PCC7120, as mentioned above, are mentioned. These genes and nucleotide sequences can be checked on the aforementioned CyanoBase or NCBI database. For example, a polynucleotide encoding Sll0822 of *Synechocystis* sp. PCC6803 can be identified as sll0822 gene (NCBI Gene ID: 953185); and a polynucleotide encoding Syn7509DRAFT_00022930 of *Synechocystis* sp. PCC7509 can be identified as syn7509DRAFT_00022930 gene (GenBank ID: ELR88577.1; SEQ ID NO: 24).

In the present invention, as an example of the gene encoding acyl-ACP synthetase to be deleted or inactivated in order to cause loss of the function of acyl-ACP synthetase, a polynucleotide encoding Slr1609 of *Synechocystis* sp. PCC6803, Syn7509DRAFT_00010940 of *Synechocystis* sp. PCC7509, Synpcc7942_0918 of *Synechococcus* sp. PCC7942, Tll1301 of *ThermoSynechococcus elongatus* BP-1, Tery_1829 of *Trichodesmium erythraeum* IMS101, AM1_5562 or AM1_2147 of *Acaryochloris mariana* MBIC11017, Cwat_5663 of *Crocosphaera watsonii* WH8501 or Alr3602 of *Anabaena* sp. PCC7120 as mentioned above, can be mentioned. These genes and nucleotide sequences thereof can be checked on the aforementioned CyanoBase or NCBI database. For example, a polynucleotide encoding Slr1609 of *Synechocystis* sp. PCC6803 can be identified as slr1609 gene (NCBI Gene ID: 953643); and a polynucleotide encoding syn7509 DRAFT_00010940 of *Synechocystis* sp. PCC7509 can be identified as syn7509DRAFT_00010940 gene (GenBank ID: ELR87398.1; SEQ ID NO:25). In the present invention, as the gene encoding acyl-ACP synthetase to be deleted or inactivated in order to cause loss of the function of acyl-ACP synthetase, slr1609 gene or syn7509DRAFT_00010940 gene is (SEQ ID NO:25) preferable; and slr1609 gene is more preferable. Furthermore, a polynucleotide having a nucleotide sequence having an identity of 40% or more with any one of the nucleotide sequences of these polynucleotides, preferably 50% or more, more preferably 60% or more, further preferably 70% or more, still further preferably 80% or more, still further preferably 90% or more, still further preferably 95% or more, still further preferably 98% or more and still further preferably 99% or more, and encoding a polypeptide having a function of synthesizing acyl-ACP, can be mentioned as an example of the gene encoding acyl-ACP synthetase to be deleted or inactivated in the present invention.

As means for deleting or inactivating a gene as mentioned above, introduction of a mutation of one or more nucleotides in the nucleotide sequence of the gene, or substitution or insertion of a different nucleotide sequence in the nucleotide sequence, or deletion of a part or whole sequence of the gene, is mentioned. As means for introducing a mutation which inhibits transcription of a gene as mentioned above, introduction of a mutation in a promoter region of the gene and inactivation of the promotor by substitution or insertion of a different nucleotide sequence, are mentioned. Examples of a specific method for introducing a mutation and for substituting or inserting a nucleotide sequence may include ultraviolet irradiation and site-specific mutagenesis, homologous recombination and SOE (splicing by overlap extension)-PCR method (Gene, 1989, 77: 61-68). As means for inhibiting the translation of a transcript as mentioned above, interference of RNA by micro RNA can be mentioned. As a protein-specific inhibitor, a specific antibody against the protein, its receptor or ligand can be mentioned.

In a preferable embodiment, the modified cyanobacterium of the present invention may further have an introduction of a heterologous gene encoding acyl-ACP thioesterase in addition to the aforementioned modification. In other words, the modified cyanobacterium according to a preferable embodiment of the present invention may be a cyanobacterium in which functions of cyAbrB and acyl-ACP synthetase are lost and which further have a heterologous gene encoding acyl-ACP thioesterase. The acyl-ACP thioesterase is an enzyme of dissociating a fatty acid chain from acyl-ACP in the fatty acid synthesis pathway. It is reported that if acyl-ACP thioesterase is introduced in a cyanobacterium, a fatty acid is cleaved out from acyl-ACP produced by fatty acid synthesis to produce a free fatty acid (Non-Patent Literature 4). In another report, it is pointed out that in order to efficiently secrete a free fatty acid produced by the function of acyl-ACP thioesterase in a cyanobacterium, it is effective to cause loss of the function of endogenous acyl-ACP synthetase gene (Plant Physiol, 2010, 152: 1598-1610). Accordingly, if a gene encoding acyl-ACP thioesterase is externally introduced to the modified cyanobacterium of the present invention, production of a fatty acid within the cell is promoted and secretory production of fatty acid by the modified cyanobacterium can be further improved.

As the gene encoding acyl-ACP thioesterase to be introduced into the modified cyanobacterium of the present invention, genes isolated from e.g., plants containing a large amount of medium-chain fatty acids in seed oil or algae capable of producing fatty acids can be mentioned. For example, a gene encoding acyl-ACP thioesterase derived from the following plant or alga: *Arabidopsis thaliana; Bradyrhizobium japonicum; Brassica napus; Cinnamonum camphorum; Capsicum chinense; Cuphea hookeriana; Cuphea lanceolata; Cuphea palustris; Coriandrum sativum* L.; *Carthamus tinctorius; Cuphea wrightii; Elaeis guineensis; Gossypium hirsutum; Garcinia mangostana; Helianthus annuus; Iris germanica; Iris tectorum; Myristica fragrans; Triticum aestivum; Ulmus Americana; Cinnamomum camphorum; Cocos nucifera;* or *Umbellularia californica* is mentioned. Alternatively, a gene encoding acyl-ACP thioesterase of *Escherichia coli* can be introduced into the modified cyanobacterium of the present invention. The heterologous gene encoding acyl-ACP thioesterase of the present invention is preferably a gene encoding acyl-ACP thioesterase (NCBI database GI: 595955) derived from *Umbellularia californica*, a gene encoding acyl-ACP thioesterase (GI: AAC49151.1) of *Cinnamomum camphorum*, a gene encoding acyl-ACP thioesterase (GI: AEM72521.1) of *Cocos nucifera* or a gene encoding acyl-ACP thioesterase (GI: AAC73596.1) of *Escherichia coli*. The genes encoding acyl-ACP thioesterase derived from the above plants, algae or *Escherichia coli* can be identified on the NCBI database. For example, acyl-ACP thioesterase (UcTE) gene derived from *Umbellularia californica* has been registered as GenBank ID: U17097 in the NCBI database. Furthermore, for example, genes encoding acyl-ACP thioesterase of *Cinnamomum camphorum* and *Cocos nucifera* have been registered as GenBank ID: U31813 and GenBank ID: JF338905, respectively. Moreover, for example, a gene encoding acyl-ACP thioesterase of E. coli K-12 strain has been registered as NCBI Gene ID: 945127.

Acyl-ACP thioesterase has a specificity to the fatty acid chain length and degree of unsaturation of a substrate, acyl-ACP (U.S. Pat. No. 5,298,421, Planta, 1993, 189: 425-432). Accordingly, a free fatty acid having a desired chain length and unsaturation degree can be produced by a cyanobacterium by changing the type of acyl ACP thioesterase to be introduced. For example, the acyl-ACP thioesterase (UcTE) derived from Umbellularia californica, as mentioned above has a substrate specificity to a C12 (chain-length) acyl group and mainly produces a C12 (chain length) free fatty acid such as lauric acid (C12: 0). For example, the acyl-ACP thioesterases of Cinnamomum camphorum and Cocos nucifera, as mentioned above have a substrate specificity to a C14 (chain length) acyl group and mainly produce a C14 (chain length) free fatty acid such as myristic acid (C14: 0). For example, the acyl-ACP thioesterase of E. coli K-12 strain as mentioned above has a substrate specificity to a C16 or C18 (chain length) acyl group and mainly produces a C16 or C18 (chain-length) free fatty acid such as palmitic acid (C16: 0), palmitoleic acid (C16: 1), stearic acid (C18: 0), oleic acid (C18: 1), linoleic acid (C18: 2) and linolenic acid (C18: 3).

The heterogeneous acyl-ACP thioesterase gene to be introduced into the modified cyanobacterium of the present invention is preferably optimized in codon in accordance with use frequency of codon in the cyanobacterium. Information on codons used in each of organisms is available from Codon Usage Database ([www.kazusa.or.jp/codon/]). For example, if the polynucleotide encoding acyl-ACP thioesterase UcTE derived from Umbellularia californica is optimized in codon in accordance with a cyanobacterium, a polynucleotide represented by SEQ ID. No. 3 can be obtained.

Therefore, preferable examples of the acyl-ACP thioesterase gene to be introduced into a cyanobacterium in the present invention may include a polynucleotide encoding acyl-ACP thioesterase UcTE derived from Umbellularia californica and having the nucleotide sequence represented by SEQ ID. No. 3 and a polynucleotide encoding a polypeptide and having a nucleotide sequence having an identity of 80% or more with the nucleotide sequence represented by SEQ ID. No. 3, preferably 90% or more, more preferably 95% or more, further preferably 98% or more and still further preferably 99% or more, and having a function of dissociating a fatty acid chain from acyl-ACP.

In introducing a heterogeneous acyl-ACP thioesterase gene into a cyanobacterium, for example, a vector such as a plasmid vector can be used. As the vector, an expression vector is preferable. For example, an expression vector containing a DNA fragment of a heterogeneous acyl-ACP thioesterase gene and a promoter for expressing the gene is constructed. As the promoter, a lac, tac or trc promoter, a promotor regarding to a derivative inducible by addition of isopropyl β-D-1-thiogalactopyranoside (IPTG) or a promotor, which is involved in expression such as Rubisco operon (rbc), a gene (psaAB) encoding a PSI reaction-center protein or a gene (psbA) encoding D1 protein of PSII and isolated from cyanobacterium, can be used; however, the promotor is not limited to these and various types of promoters which function in cyanobacteria can be used. Furthermore, in the above expression vectors, a marker gene (for example, a gene resistant to a drug such as kanamycin, chloramphenicol, spectinomycin or erythromycin) is further integrated therein for selecting a host having the vector properly introduced therein. An expression vector as mentioned above is introduced into a parent cyanobacterium or the modified cyanobacterium of the present invention by known means to transform the cyanobacterium. As a method for introducing the vector into a cyanobacterium, a general method such as a natural transformation method, an electroporation method and a conjugation method can be used. A cyanobacterium transformed is cultured in a selection medium, for example, an antibiotic-containing medium, to successfully obtain transformants having the desired trait.

In a preferable embodiment, a heterogeneous acyl-ACP thioesterase gene is introduced in the region of an endogenous acyl-ACP synthetase gene on the genome of a cyanobacterium. In this way, the function of acyl-ACP synthetase in the cyanobacterium is lost; at the same time, an ability to express heterogeneous acyl-ACP thioesterase is provided. For example, a DNA fragment of a heterogeneous acyl-ACP thioesterase gene with a DNA fragment of the acyl-ACP synthetase gene region added to both ends is constructed by the SOE-PCR method (Gene, 1989, 77: 61-68) and introduced into a vector. The vector is introduced into a cyanobacterium to cause homologous recombination on the genome with the acyl-ACP synthetase gene region. In this manner, a modified cyanobacterium having the heterogeneous acyl-ACP thioesterase gene introduced in the acyl-ACP synthetase gene region on the genome, can be obtained. In another embodiment, a heterogeneous acyl-ACP thioesterase gene may be introduced into a region (neutral site) of the genome of a cyanobacterium where any gene, if introduced, will not damage the cyanobacterium.

(3. Method for Producing Fatty Acid)

The modified cyanobacterium of the present invention can be produced in the aforementioned procedure. The modified cyanobacterium of the present invention is improved in fatty acid secretory productivity. Accordingly, if the modified cyanobacterium of the present invention is cultured in suitable conditions and then, the fatty acid secreted there is recovered, a microbiological fatty acid can be efficiently produced. The fatty acids which are secreted and produced by cyanobacteria in accordance with the fatty acid production method of the present invention may be free fatty acids, preferably a free fatty acid rich in lauric acid (C12: 0).

Cyanobacteria can be cultured generally based on a liquid culture using a BG-11 medium (J Gen Microbiol., 1979, 111: 1-61) or a modified method. The culture for producing a fatty acid may be performed in a period during which bacterial cells are sufficiently grown to accumulate fatty acids in high concentrations, for example, from 7 to 45 days, preferably from 10 to 30 days, and more preferably from 14 to 21 days, by an aeration/spinner culture or shaking culture.

By the above culture, a cyanobacterium produces a fatty acid and secretes the fatty acid in the culture. The fatty acid secreted may be recovered by removing a solid content such as cells from the culture by filtration and/or centrifugation, collecting the remaining liquid component, recovering or purifying the fatty acid by e.g., a chloroform/methanol extraction method, a hexane extraction method or an ethanol extraction method. In a large-scale production, the fatty acid can be recovered by collecting an oil content from the culture from which cells are removed, by squeezing or extracting, and subjecting the oil content to general purification such as degumming, deacidifying, bleaching, dewaxing and deodorizing. In the fatty acid production method of the present invention, since a fatty acid is secreted outside the cyanobacterial cells, it is not necessary to destroy the cells for recovering the fatty acid. The remaining cells after the fatty acid is recovered can be repeatedly used for fatty acid production.

The fatty acid obtained by the fatty acid production method using the modified cyanobacterium of the present invention can be used not only as foods but also as raw materials for emulsifiers which are blended in e.g., cosmetics, cleansing agents such as soaps or detergents, fiber treatment agents, hair rinses or disinfectants and preservatives.

(4. Exemplary Embodiments)

As other exemplary embodiments of the present invention mentioned above, the following compositions, production methods, uses or methods will be disclosed in the specification; however, the present invention is not limited by these embodiments.

<1> A method for producing a modified cyanobacterium, comprising causing loss of functions of an AbrB-like transcriptional regulator and acyl-ACP synthetase in the cyanobacterium.

<2> A method for improving fatty acid secretory productivity in a cyanobacterium, comprising causing loss of functions of an AbrB-like transcriptional regulator and acyl-ACP synthetase in the cyanobacterium.

<3> A modified cyanobacterium having lost functions of an AbrB-like transcriptional regulator and acyl-ACP synthetase.

<4> The method according to <1>, preferably comprising deleting or inactivating a gene encoding an AbrB-like transcriptional regulator and a gene encoding acyl-ACP synthetase in the cyanobacterium.

<5> The method according to <2>, preferably comprising deleting or inactivating a gene encoding an AbrB-like transcriptional regulator and a gene encoding acyl-ACP synthetase in the cyanobacterium.

<6> The modified cyanobacterium according to <3>, preferably comprising deleting or inactivating a gene encoding an AbrB-like transcriptional regulator and a gene encoding acyl-ACP synthetase.

<7> The method according to <1> or <4>, preferably further comprising introducing a heterologous gene encoding acyl-ACP thioesterase into the cyanobacterium.

<8> The method according to <2> or <5>, preferably further comprising introducing a heterologous gene encoding acyl-ACP thioesterase into the cyanobacterium.

<9> The modified cyanobacterium according to <3> or <6>, preferably comprising a heterologous gene encoding acyl-ACP thioesterase.

<10> In any one of <4> to <9>, the gene encoding the AbrB-like transcriptional regulator is preferably selected from the group consisting of following (1) to (3):

(1) a polynucleotide encoding the AbrB-like transcriptional regulator shown in FIG. 1;

(2) a polynucleotide encoding a protein belonging to a group B of the cyAbrB family; preferably a polynucleotide encoding a protein selected from the group consisting of Sll0822, Syn7509DRAFT_00022930, Synpcc7942_2255, Tll2172, Tery1859, AM1_4418, Cwat2079 and All2080; and (3) a polynucleotide having a nucleotide sequence having an identity of 40% or more, preferably 50% or more, more preferably 60% or more, further preferably 70% or more, still further preferably 80% or more, still further preferably 90% or more, still further preferably 95% or more, still further preferably 98% or more and still further preferably 99% or more with any one of the nucleotide sequences of polynucleotides shown in (1) and (2) above, and encoding a polypeptide having AbrB transcriptional regulatory function.

<11> In <10>, the gene encoding an AbrB-like transcriptional regulator is preferably sll0822 gene or syn7509DRAFT_00022930 gene, and more preferably sll0822 gene.

<12> In any one of <4> to <11>, the gene encoding acyl-ACP synthetase is preferably selected from the group consisting of the following (1) and (2):

(1) a polynucleotide encoding a protein selected from the group consisting of Slr1609, Syn7509DRAFT_00010940, Synpcc7942_0918, Tll1301, Tery_1829, AM1_5562, AM1_2147, Cwat_5663 and Alr3602; and (2) a polynucleotide having a nucleotide sequence having an identity of 40% or more, preferably 50% or more, more preferably 60% or more, further preferably 70% or more, still further preferably 80% or more, still further preferably 90% or more, still further preferably 95% or more, still further preferably 98% or more and still further preferably 99% or more with any one of the nucleotide sequences of the polynucleotides shown in (1) above, and encoding a polypeptide having a function of synthesizing acyl-ACP.

<13> In <12>, the gene encoding acyl-ACP synthetase is preferably slr1609 gene or syn7509DRAFT_00010940 gene and more preferably slr1609 gene.

<14> In any one of <7> to <13>, preferably, the heterologous gene encoding acyl-ACP thioesterase is selected from the group consisting of the following (1) and (2):

(1) a polynucleotide having the nucleotide sequence represented by SEQ ID. No. 3; and (2) a polynucleotide having a nucleotide sequence having an identity of 804 or more, preferably 904 or more, more preferably 95% or more, further preferably 98% or more and still further preferably 99% or more with the nucleotide sequence represented by SEQ ID. No. 3, and encoding a polypeptide having a function of dissociating a fatty acid chain from acyl-ACP.

<15> In any one of <7> to <13>, preferably, the heterologous gene encoding acyl-ACP thioesterase is a gene encoding acyl-ACP thioesterase of *Cinnamomum camphorum* or *Cocos nucifera* (*Cocos nucifera*).

<16> In any one of <7> to <13>, preferably, the heterologous gene encoding acyl-ACP thioesterase is a gene encoding acyl-ACP thioesterase of *Escherichia coli* K-12.

<17> In any one of <7> to <16>, preferably, the heterologous gene encoding acyl-ACP thioesterase is introduced in the region of the gene encoding acyl-ACP synthetase or a neutral site in the genome sequence of the cyanobacterium.

<18> In any one of <1> to <17>, the cyanobacterium is preferably a cyanobacterium of *Synechocystis, Synechococcus, Thermosynechococcus, Trichodesmium, Acaryochloris, Crocosphaera* or *Anabaena*;

more preferably, *Synechocystis* sp. PCC6803, *Synechocystis* sp. PCC7509, *Synechocystis* sp. PCC6714, *Synechococcus* sp. PCC7942, *ThermoSynechococcus elongates* BP-1, *Trichodesmium erythraeum* IMS101, *Acaryochloris mariana* MBIC11017, *Crocosphaera watsonii* WH8501 or *Anabaena* sp. PCC7120; and further preferably, *Synechocystis* sp. PCC6803, *Synechocystis* sp. PCC6714 or *Synechocystis* sp. PCC7509.

<19> A method for producing a fatty acid, comprising culturing the modified cyanobacterium produced by the method according to any one of <1>, <4>, <7> and <10> to <18>.

<20> A method for producing a fatty acid, comprising culturing the modified cyanobacterium according to any one of <3>, <6>, <9> and <10> to <18>.

<21> The method according to <19> or <20>, in which preferably, a gene encoding acyl-ACP thioesterase derived from *Umbellularia californica* is introduced in the modified cyanobacterium and C12 (chain length) free fatty acid is mainly produced.

<22> The method according to <19> or <20>, in which preferably, a gene encoding acyl-ACP thioesterase derived from *Cinnamomum camphorum* or *Cocos nucifera* is introduced in the modified cyanobacterium and C14 (chain length) free fatty acid is mainly produced.

<23> The method according to <19> or <20>, in which preferably, a gene encoding acyl-ACP thioesterase derived from *Escherichia coli* K-12 is introduced in the modified cyanobacterium and C16 or C18 (chain length) free fatty acid is mainly produced.

EXAMPLE

Now, the present invention will be more specifically described based on Examples; however, the present invention is not limited to these.

Reference Example 1

Culture of Cyanobacterial Strain

In the following Examples, a cyanobacterial strain was cultured in a 100 mL conical flask containing 50 mL of modified BG-11 under a predetermined illumination (40 µE·m$^{-2}$·sec$^{-1}$) at 30° C. by using a rotary shaker (120 rpm). When transformants were selected by culturing, an appropriate antibiotic was added to a medium so as to satisfy the following final concentration: final concentration of chloramphenicol: 25 µg/mL or final concentration of spectinomycin or kanamycin: 20 µg/mL. The composition of the modified BG-11 medium is shown in Table 1 below.

TABLE 1

Composition of stock solution

| A solution | |
|---|---|
| Citric acid•H$_2$O | 0.33 g |
| Ferric ammonium citrate | 0.3 g |
| Na$_2$EDTA | 0.05 g |
| total | 100 ml |
| B solution | |
| NaNO$_3$ | 30 g |
| K$_2$HPO$_4$ | 0.78 g |
| MgSO$_4$•7H$_2$O | 1.5 g |
| total | 100 ml |
| C solution CaCl$_2$•2H$_2$O | 1.9 g/100 ml |
| D solution Na$_2$CO$_3$ | 2 g/100 ml |
| E solution (the following substances are added) [H$_3$BO$_3$ 2.86 g, MnCl$_2$•4H$_2$O 1.81 g, ZnSO$_4$•7H$_2$O 0.22 g, CuSO$_4$•5H$_2$O 0.08 g, Na$_2$MoO$_4$ 0.021 g, Co (NO$_3$)•6H$_2$O 0.0494 g, conc. H$_2$SO$_4$ single drop, H$_2$O]/1000 ml | |

| Modified BG-11 broth Stock solution | |
|---|---|
| A solution | 2 ml |
| B solution | 50 ml |
| C solution | 2 ml |
| D solution | 1 ml |
| E solution | 1 ml |
| 1.0M TES-KOH (pH 8.2) | 5 ml |
| total | 1000 ml |

Example 1

Construction of a cyAbrB/Acyl-ACP Synthetase Double Knockout Modified Cyanobacterial Strain (1. Construction of ΔrecJ Strain Derived from Synechocystis sp. PCC6803)

In Synechocystis sp. PCC6803, which was a unicellular and photoheterotrophic cyanobacterium, an exonuclease gene, recJ (sll1354) was destroyed to obtain a ΔrecJ strain. It is reported that if recJ gene is destroyed, gene recombination efficiency is improved (FEMS Microbiol Lett, 2002, 206: 215-219). The gene recombination efficiency is improved by using the ΔrecJ strain as a parent strain and a recombinant can be easily obtained. However, even if a ΔrecJ strain is not used as a parent strain, the modified cyanobacterium of the present invention having cyAbrB/ acyl-ACP synthetase double knockouts, can be constructed. Even if recJ is destroyed, the fatty acid productivity of the modified cyanobacterium of the present invention will not be substantially influenced. To describe construction more specifically, a recJ gene coding region was divided into 2 DNA fragments by using the genome DNA of Synechocystis sp. PCC6803 strain as a template and a primer set of recJ-F and Cm/recJ-R or Cm/recJ-F and recJ-R shown in Table 2. Furthermore, by using a primer set of Cm-F and Cm-R shown in Table 2, DNA sequence of 1333 bp having a chloramphenicol resistant marker gene (cat) was amplified by PCR from pACYC184 plasmid. Then, by using a solution containing the two recJ gene fragments prepared and the cat fragment, as a template, fusion PCR was performed by using recJ-F and recJ-R primers shown in Table 2 to obtain a construct having an insert of the cat fragment in recJ gene coding regions. Synechocystis sp. PCC6803 wild-type strain was transformed with the obtained construct to obtain ΔrecJ strain (recJ gene was destroyed) having chloramphenicol resistance.

(2. Providing Fatty Acid Secretory Ability to ΔrecJ Strain)

Secretory production of a fatty acid by Synechocystis sp. PCC6803 in a broth can be attained by causing loss of the function of endogenous acyl-ACP synthetase (slr1609) (Plant Physiol, 2010, 152: 1598-1610). It was reported that fatty acid production is promoted by introducing a gene encoding acyl-ACP thioesterase into PCC6803 strain (Non-Patent Literature 4). In this example, a spectinomycin resistant gene was inserted in the coding region of slr1609 gene encoding acyl-ACP synthetase on the genome of Synechocystis sp. PCC6803 to inactivate the slr1609 gene. In this manner, the function of acyl-ACP synthetase was lost and a modified strain improved in fatty acid production was prepared. Furthermore, an acyl-ACP thioesterase (UcTE) gene derived from Umbellularia californica (codon was optimized in accordance with Synechocystis sp. PCC6803) was inserted into the slr1609 coding region to prepare a modified strain further improved in fatty acid productivity. A method for preparing the modified strain will be more specifically described below.

From genome DNA of Synechocystis sp. PCC6803 strain, a gene fragment of slr1609 (2049 bp) was amplified by using primers slr1609f-F and slr1609r-R shown in Table 2, and cloned between HincII sites in pUC118 plasmid (manufactured by Takara Bio Inc.) to obtain pUC118-slr1609 plasmid.

PCR using pDG1726 plasmid (Guerout-Fleury et al., Gene, 1995, 167: 335-336) as a template and primers slr1609/sp-F and slr1609/sp-R shown in Table 2, was carried out to obtain a spectinomycin resistant marker gene fragment (sp fragment: SEQ ID. No. 1). Next, PCR using the pUC118-slr1609 plasmid as a template and primers slr1609f-R and slr1609r-F shown in Table 2, was carried out to obtain a linear DNA fragment having a deletion of 242 bp-region in slr1609 gene coding region. This fragment was ligated to the sp fragment by In-Fusion (registered trade mark) PCR cloning method (Clontech) to obtain pUC118-slr1609::sp plasmid containing a DNA sequence of slr1609 gene coding region having the sp fragment inserted therein.

PCR using the pUC118-slr1609::sp plasmid as a template and primers slr1609-R and Sp-F shown in Table 2, was carried out to obtain a linear plasmid. Using primers slr1609/ psbA2-F and psbA2/UcTE-R shown in Table 2, a promoter region fragment (SEQ ID. No. 2) of psbA2 gene derived from Synechocystis sp. PCC6803 was amplified by PCR. The acyl-ACP thioesterase (UcTE) gene fragment (UcTE fragment: SEQ ID. No. 3) derived from Umbellularia californica was prepared by artificially synthesizing a sequence, the codon of which was optimized in accordance with Synechocystis sp. PCC6803, described in Non-Patent Literature 4, and amplifying the sequence by PCR using primers of UcTE-F and UcTE/sp-R shown in Table 2. To the linear plasmid obtained above, the psbA2 promoter region fragment and the UcTE fragment were cloned by In-Fusion (registered trade mark) PCR cloning method (Clontech) to obtain pUC118-slr1609::psbA2-UcTE-sp plasmid having an insertion, which consists of the psbA2 promoter region fragment, UcTE fragment and sp fragment arranged in this order, in the slr1609 gene coding region.

The ΔrecJ strain prepared in Section 1 was transformed with the resultant pUC118-slr1609::sp plasmid and selected based on spectinomycin resistance to obtain ΔrecJΔslr1609::sp strain in which acyl-ACP synthetase gene slr1609 on the genome was inactivated. Furthermore, another ΔrecJ strain was transformed with pUC118-slr1609::psbA2-UcTE-sp plasmid and selected based on spectinomycin resistance. In this manner, ΔrecJΔslr1609::UcTE strain in which acyl-ACP synthetase gene slr1609 was inactivated; at the same time, acyl-ACP thioesterase expressional potency was provided, was obtained by introducing the acyl-ACP thioesterase (UcTE) gene (codon optimized) in the acyl-ACP synthetase slr1609 gene coding region on the genome.

(3. Construction of cyAbrB Knockout Strain)

A genomic region (900 bp) of Synechocystis sp. PCC6803 (corresponding to the region of genome nucleotide No. 2862739 to 2861840 in the CyanoBase) containing gene sll0822 encoding an AbrB-like transcriptional regulator was amplified by using the genome DNA of Synechocystis sp. PCC6803 strain as a template and primers 0822delF and 0822delR shown in Table 2.

The resultant PCR product was cloned to pT7Blue T-vector (Novagen) and a kanamycin resistant marker gene (cleaved from pRL161 plasmid by HincII treatment) was inserted to the StyI site of the sll0822 gene. The obtained construct was inserted to each of ΔrecJΔslr1609::sp strain and ΔrecJΔslr1609::UcTE strain prepared in Section 2. Screening was made based on kanamycin resistance to obtain double-gene knockout strains (defective strains), namely ΔrecJΔsll0822Δslr1609::sp strain and ΔrecJΔsll10822Δslr1609::UcTE strain.

TABLE 2

| Primer | Sequence | SEQ. ID. No. |
|---|---|---|
| recJ-F | 5'-ATGGCCCAATTTCGTTGGC-3' | 4 |
| Cm/recJ-R | 5'-AAAAGCACCGCCGGACATGTTGGGGCACTGTGGG-3' | 5 |
| recJ-R | 5'-TCATGGCTTGTCGGGTAC-3' | 6 |
| Cm/recJ-F | 5'-CGGTAAGCGCTTCGTTAATACACCAGCTTTCGGGTAACG-3' | 7 |
| Cm-F | 5'-ATGTCCGGCGGTGCTTTT-3' | 8 |
| Cm-R | 5'-GTATTAACGAAGCGCTAACCG-3' | 9 |
| slr1609f-F | 5'-ATGGCGCTCAATCCAGGATAAAG-3' | 10 |
| slr1609r-R | 5'-AAGTTTGGGTTACCACTGGTCG-3' | 11 |
| slr1609f-R | 5'-TTTCTAGGGAGTGCCAACAGG-3' | 12 |
| slr1609r-F | 5'-AACCTGAGCTTGAACCATCTCC-3' | 13 |
| slr1609/sp-F | 5'-GGCACTCCCTAGAAAATCGATTTTCGTTCGTG-3' | 14 |
| slr1609/sp-R | 5'-GTTCAAGCTCAGGTTCATATGCAAGGGTTTATTG-3' | 15 |
| slr1609-R | 5'-AACCTGAGCTTGAACCATCTCC-3' | 16 |
| Sp-F | 5'-ATCGATTTTCGTTCGTG-3' | 17 |
| slr1609/psbA2-F | 5'-GGCACTCCCTAGAAAATTATTTCATCTCCATTGTCCC-3' | 18 |
| psbA2/UcTE-R | 5'-TAGGAATTATAACCATAGGTTATAATTCCTTATGTATTTG-3' | 19 |
| UcTE-F | 5'-ATGGCTACCACCTCTTTAGCTTC-3' | 20 |
| UcTE/sp-R | 5'-GAACGAAAATCGATTTACACGCGCGGTTCGGCGG-3' | 21 |
| 0822delF | 5'-CGTCGCAGGGTAATCAAC-3' | 22 |
| 0822delR | 5'-GTATGAGGAAATCAACAG-3' | 23 |

Example 2

Improvement of Fatty Acid Secretory Productivity of Modified Cyanobacterial Strain (1. Culture of Modified Strain)

ΔrecJΔslr1609::sp strain, ΔrecJΔsll10822Δslr1609::sp strain, ΔrecJΔslr1609::UcTE strain and ΔrecJΔsll10822Δslr1609::UcTE strain prepared in Example 1 were cultured at an initial cell density OD730 of 0.2 in a broth for two weeks in the conditions described in Reference Example 1.

(2. Analysis of Fatty Acid Composition)

After completion of the culture, NaHPO₄ (1 g) and 10 μL of C15 fatty acid (7-pentadecanone; 5 nmol/μL) serving as an internal standard and dissolved in toluene were added to each broth (50 mL). To this solution, hexane (10 mL) was added. After sufficiently stirred, the mixture was allowed to stand still for 10 minutes and subsequently centrifuged at 2500 rpm for 10 minutes at room temperature. Thereafter, an upper layer (hexane layer) was taken and transferred to an eggplant-shaped flask. Subsequently, to the lower layer separated by centrifugation, hexane (5 mL) was added. The mixture was stirred, allowed to stand still and centrifuged in the same manner as above. This operation was further repeated twice. The upper layers obtained were combined and concentrated under reduced pressure to obtain a dry sample. To an eggplant-shaped flask, a 5% methanol solution of hydrochloric acid (3 mL) was added and the dry sample was dissolved. The whole volume of the solution was transferred to a screw-top test tube and treated at a high temperature of 80° C. for 3 hours to perform methyl esterification of the fatty acid. To the resulting sample, hexane (3 mL) was further added. After the mixture was sufficiently stirred and allowed to stand still for 5 minutes, the upper layer was taken and appropriately concentrated and subjected to gas chromatographic analysis by using a gas chromatography apparatus, GC-2014 (SHIMADZU) in the following conditions.

[Capillary column: ULBON HR-SS-10 25 m×0.25 mmφ (SHIMADZU), moving phase: high purity helium, the flow rate in the column: 1.98 mL/min, temperature raising program: 170° C. (30 minutes)→raising temperature at a rate of 10° C./min→220° C. (5 minutes), equilibration time: 3 minutes, inlet: split injection (split ratio: 10:1), pressure 278 kPa, 24.8 mL/min, injection volume: 2 μL, vial washing: hexane, detector's temperature: 250° C.]

Based on the peak area of waveform data obtained by gas chromatographic analysis, the amounts of methyl esters of individual fatty acids secreted in the broth were quantified. Corrections among the samples were conducted based on comparison between individual peak areas (obtained by measurement) to the peak area of the internal standard, 7-pentadecanone. The amount of free fatty acid per broth (1 liter) was calculated and normalized by the amount of cyanobacterial cells (OD730) contained in the broth and measured in advance, to obtain fatty-acid secretion amount per cell. Culture and chromatographic analysis were repeated three times with respect to each modified strain and fatty acid secretion amounts were calculated and averaged.

The results are shown in FIGS. 2 to 5. In the modified cyanobacterium strains, ΔrecJΔsll0822Δslr1609::sp having double knockouts of cyAbrB and acyl-ACP synthetase, the fatty acid secretion amount per broth was improved by a factor of 2.40 (FIG. 2) and the fatty acid secretion amount per cell was improved by a factor of 2.35 (FIG. 3), compared to those of strain ΔrecJΔslr1609::sp having a single knockout of acyl-ACP synthetase.

The fatty acid secretion amount by ΔrecJΔsll10822Δslr1609::UcTE strain prepared by further introducing acyl-ACP thioesterase gene to the double knockout strain, was improved by a factor of 2.26 per broth (FIG. 4) and improved about by a factor of 2.13 per cell (FIG. 5), compared to that of acyl-ACP thioesterase gene introduced single-knockout strain ΔrecJΔslr1609::UcTE. Furthermore, the fatty acid secretion amount by acyl-ACP thioesterase gene introduced double knockout strain ΔrecJΔsll10822Δslr1609::UcTE was improved by a factor of 1.65 per broth and improved by a factor of 1.84 per cell compared to those of ΔrecJΔsll10822Δslr1609::sp strain with no acyl-ACP thioesterase gene introduced therein.

From the above results, it was found that bacterial fatty acid secretory production is accelerated and the amount of fatty acid secretory production per broth is greatly improved by causing loss of the functions of an AbrB-like transcriptional regulator and acyl-ACP synthetase in cyanobacteria.

The invention claimed is:

1. A method for producing a modified cyanobacterium, comprising causing loss of function of an AbrB-like transcriptional regulator and acyl-ACP synthetase in a cyanobacterium, wherein the AbrB-like transcriptional regulator belongs to group B of the cyAbrB family.

2. The method for producing a modified cyanobacterium according to claim 1, comprising deleting or inactivating a gene encoding an AbrB-like transcriptional regulator and a gene encoding acyl-ACP synthetase.

3. The method for producing a modified cyanobacterium according to claim 2, wherein the gene encoding an AbrB-like transcriptional regulator is the sll0822 gene or a gene having the sequence of SEQ ID No: 24.

4. The method for producing a modified cyanobacterium according to claim 2, wherein the gene encoding acyl-ACP synthetase is the slr1609 gene or a gene having the sequence of SEQ ID No: 25.

5. The method for producing a modified cyanobacterium according to claim 1, further comprising introducing a heterologous gene encoding acyl-ACP thioesterase into the cyanobacterium.

6. The method for producing a modified cyanobacterium according to claim 5, wherein the gene encoding acyl-ACP thioesterase is a gene encoding acyl-ACP thioesterase derived from *Umbellularia californica*.

7. The method for producing a modified cyanobacterium according to claim 5, wherein the gene encoding acyl-ACP thioesterase is introduced into a region of the gene encoding acyl-ACP synthetase.

8. The method for producing a modified cyanobacterium according to claim 1, wherein the cyanobacterium belongs to *Synechocystis, Synechococcus, Thermosynechococcus* or *Anabaena*.

9. A method for producing a fatty acid, comprising culturing the modified cyanobacterium produced by the method according to claim 1.

10. A method for improving fatty acid secretory productivity in a cyanobacterium, comprising causing loss of function of an AbrB-like transcriptional regulator and acyl-ACP synthetase in the cyanobacterium, wherein the AbrB-like transcriptional regulator belongs to group B of the cyAbrB family.

11. The method for improving fatty acid secretory productivity in a cyanobacterium according to claim 10, comprising deleting or inactivating a gene encoding an AbrB-like transcriptional regulator and a gene encoding acyl-ACP synthetase.

12. The method for improving fatty acid secretory productivity in a cyanobacterium according to claim 11, wherein the gene encoding the AbrB-like transcriptional regulator is the sll0822 gene or a gene having the sequence of SEQ ID No: 24.

13. The method for improving fatty acid secretory productivity in a cyanobacterium according to claim 11, wherein the gene encoding acyl-ACP synthetase is the slr1609 gene or a gene having the sequence of SEQ ID No: 25.

14. The method for improving fatty acid secretory productivity in a cyanobacterium according to claim 10, further comprising introducing a heterologous gene encoding acyl-ACP thioesterase into the cyanobacterium.

15. The method for improving fatty acid secretory productivity in a cyanobacterium according to claim 14, wherein the gene encoding acyl-ACP thioesterase is a gene encoding acyl-ACP thioesterase derived from *Umbellularia californica*.

16. The method for improving fatty acid secretory productivity in a cyanobacterium according to claim 14, wherein the gene encoding acyl-ACP thioesterase is introduced into a region of the gene encoding acyl-ACP synthetase.

17. The method for improving fatty acid secretory productivity in a cyanobacterium according to claim 10, wherein the cyanobacterium belongs to *Synechocystis, Synechococcus, Thermosynechococcus* or *Anabaena*.

18. A modified cyanobacterium having lost functions of an AbrB-like transcriptional regulator and acyl-ACP synthetase, wherein the AbrB-like transcriptional regulator belongs to group B of the cyAbrB family.

19. The modified cyanobacterium according to claim 18, wherein a gene encoding an AbrB-like transcriptional regulator and a gene encoding acyl-ACP synthetase are deleted or inactivated.

20. The modified cyanobacterium according to claim 19, wherein the gene encoding the AbrB-like transcriptional regulator is the sll0822 gene or a gene having the sequence of SEQ ID No: 24.

21. The modified cyanobacterium according to claim 19, wherein the gene encoding the acyl-ACP synthetase is the slr1609 gene or a gene having the sequence of SEQ ID No: 25.

22. The modified cyanobacterium according to claim 18, further comprising a heterologous gene encoding acyl-ACP thioesterase.

23. The modified cyanobacterium according to claim 22, wherein the gene encoding acyl-ACP thioesterase is a gene encoding acyl-ACP thioesterase derived from *Umbellularia californica*.

24. The modified cyanobacterium according to claim 22, wherein the gene encoding acyl-ACP thioesterase is introduced into a region of the gene encoding acyl-ACP synthetase.

25. The modified cyanobacterium according to claim 18, belonging to *Synechocystis, Synechococcus, ThermoSynechococcus* or *Anabaena*.

26. A method for producing a fatty acid, comprising culturing the modified cyanobacterium according to claim 18.

* * * * *

SEQUENCE LISTING

<160> NUMBER OF SEQ ID NOS: 25

<210> SEQ ID NO 1
<211> LENGTH: 1158
<212> TYPE: DNA
<213> ORGANISM: Enterococcus faecalis

<400> SEQUENCE: 1

```
atcgattttc gttcgtgaat acatgttata ataactataa ctaataacgt aacgtgactg      60
gcaagagata ttttaaaac aatgaatagg tttacactta ctttagtttt atggaaatga     120
aagatcatat catatataat ctagaataaa attaactaaa ataattatta tctagataaa     180
aaatttagaa gccaatgaaa tctataaata aactaaatta agtttattta attaacaact     240
atggatataa aataggtact aatcaaaata gtgaggagga tatatttgaa tacatacgaa     300
caaattaata aagtgaaaaa aatacttcgg aaacatttaa aaaataacct tattggtact     360
tacatgtttg gatcaggagt tgagagtgga ctaaaaccaa atagtgatct tgactttta     420 gtcgtcgtat ctgaaccatt gacagatcaa agtaaagaaa tacttataca aaaaattaga     480
cctatttcaa aaaaaatagg agataaaagc aacttacgat atattgaatt aacaattatt     540
attcagcaag aaatggtacc gtggaatcat cctcccaaac aagaatttat ttatggagaa     600
```

```
tggttacaag agctttatga acaaggatac attcctcaga aggaattaaa ttcagattta    660
accataatgc tttaccaagc aaaacgaaaa aataaaagaa tatacggaaa ttatgactta    720
gaggaattac tacctgatat tccatttcct gatgtgagaa gagccattat ggattcgtca    780
gaggaattaa tagataatta tcaggatgat gaaaccaact ctatattaac tttatgccgt    840
atgattttaa ctatggacac gggtaaaatc ataccaaaag atattgcggg aaatgcagtg    900
gctgaatctt ctccattaga acatagggag agaattttgt tagcagttcg tagttatctt    960
ggagagaata ttgaatggac taatgaaaat gtaaatttaa ctataaacta tttaaataac   1020
agattaaaaa aattataaaa aaattgaaaa aatggtggaa acacttttt caattttttt    1080 gttttattat ttaatatttg ggaaatattc attctaattg gtaatcagat tttagaaaac   1140
aataaaccct tgcatatg                                                 1158

<210> SEQ ID NO 2
<211> LENGTH: 295
<212> TYPE: DNA
<213> ORGANISM: Synechocystis sp. PCC6803

<400> SEQUENCE: 2
attatttcat ctccattgtc cctgaaaatc agttgtgtcg cccctctaca cagcccagaa     60
ctatggtaaa ggcgcacgaa aaaccgccag gtaaactctt ctcaaccccc aaaacgccct    120
ctgtttaccc atggaaaaaa cgacaattac aagaaagtaa aacttatgtc atctataagc    180
ttcgtgtata ttaacttcct gttacaaagc tttacaaaac tctcattaat cctttagact    240
aagtttagtc agttccaatc tgaacatcga caaatacata aggaattata accat         295

<210> SEQ ID NO 3
<211> LENGTH: 1149
<212> TYPE: DNA
<213> ORGANISM: Umbellularia californica

<400> SEQUENCE: 3
atggctacca cctctttagc ttccgccttt tgctcgatga aagctgtaat gttagctcgt     60
gatggtcggg gtatgaaacc tcgtagtagt gatttgcaac tccgtgcggg aaatgcgcct    120
acctctttga aaatgatcaa tgggaccaaa ttcagttata cggagagctt gaaacggttg    180
cctgattgga gcatgctctt tgctgttatc accaccatct tttcggctgc tgagaaacaa    240
tggactaatc tagagtggaa gccgaaaccg aagctacccc agttgcttga tgatcatttt    300
ggactgcatg ggttagtttt ccggcgcacc tttgccatcc ggtctatga agttggacct    360 gatcgctcca cctctattct ggctgttatg aatcatatgc aggaggctac ccttaatcat    420
gcgaaaagtg tgggaattct aggagatgga ttcgggacga cgctagagat gagtaagcgg    480
gatctgatgt gggttgttcg gcgcacgcat gttgctgttg aacggtaccc tacttggggt    540
gatactgtag aagtagagtg ctggattggt gcttctggaa ataatggcat gcgtcgtgat    600
ttccttgtcc gggactgcaa aaccggcgaa attcttactc gctgtaccag cctttcggtg    660
ctgatgaata ctcgcactcg tcgtttgtcc accattcctg atgaagttcg tggtgaaata    720
gggcctgctt tcatcgataa tgttgctgtg aaagacgatg aaattaagaa actacaaaaa    780
ctcaatgata gcactgccga ttatattcaa ggaggtttga ccccctcgttg gaatgatttg    840 gatgtcaatc aacatgttaa caacctcaaa tacgttgcct gggttttga gaccgtcccc    900 gattccatct ttgagagtca tcatatttcc agcttcactc ttgaatatcg tcgtgagtgt    960
```

```
acccgtgata gcgtgctgcg gtccctgacc actgtctctg gtggctcgtc ggaggctggg    1020
ttagtttgcg atcatttgct ccaacttgaa ggtgggtctg aggtattgcg tgccagaact    1080
gagtggcggc ctaaacttac cgatagtttc cgcggcatta gtgttattcc cgccgaaccg    1140
cgcgtgtaa                                                            1149
```

```
<210> SEQ ID NO 4
<211> LENGTH: 19
<212> TYPE: DNA
<213> ORGANISM: Artificial sequence
<220> FEATURE:
<223> OTHER INFORMATION: Oligonucleotide as PCR primer

<400> SEQUENCE: 4
atggcccaat tcgttggc                                                    19

<210> SEQ ID NO 5
<211> LENGTH: 34
<212> TYPE: DNA
<213> ORGANISM: Artificial sequence
<220> FEATURE:
<223> OTHER INFORMATION: Oligonucleotide as PCR primer

<400> SEQUENCE: 5
aaaagcaccg ccggacatgt tggggcactg tggg                                  34

<210> SEQ ID NO 6
<211> LENGTH: 18
<212> TYPE: DNA
<213> ORGANISM: Artificial sequence
<220> FEATURE:
<223> OTHER INFORMATION: Oligonucleotide as PCR primer

<400> SEQUENCE: 6
tcatggcttg tcgggtac                                                    18

<210> SEQ ID NO 7
<211> LENGTH: 39
<212> TYPE: DNA
<213> ORGANISM: Artificial sequence
<220> FEATURE:
<223> OTHER INFORMATION: Oligonucleotide as PCR primer

<400> SEQUENCE: 7
cggtaagcgc ttcgttaata caccagcttt cgggtaacg                             39

<210> SEQ ID NO 8
<211> LENGTH: 18
<212> TYPE: DNA
<213> ORGANISM: Artificial sequence
<220> FEATURE:
<223> OTHER INFORMATION: Oligonucleotide as PCR primer

<400> SEQUENCE: 8
atgtccggcg gtgctttt                                                    18

<210> SEQ ID NO 9
<211> LENGTH: 21
<212> TYPE: DNA
<213> ORGANISM: Artificial sequence
<220> FEATURE:
<223> OTHER INFORMATION: Oligonucleotide as PCR primer

<400> SEQUENCE: 9
gtattaacga agcgctaacc g                                                21
```

<210> SEQ ID NO 10
<211> LENGTH: 23
<212> TYPE: DNA
<213> ORGANISM: Artificial sequence
<220> FEATURE:
<223> OTHER INFORMATION: Oligonucleotide as PCR primer

<400> SEQUENCE: 10
atggcgctca atccaggata aag                                    23

<210> SEQ ID NO 11
<211> LENGTH: 22
<212> TYPE: DNA
<213> ORGANISM: Artificial sequence
<220> FEATURE:
<223> OTHER INFORMATION: Oligonucleotide as PCR primer

<400> SEQUENCE: 11
aagtttgggt taccactggt cg                                     22

<210> SEQ ID NO 12
<211> LENGTH: 21
<212> TYPE: DNA
<213> ORGANISM: Artificial sequence
<220> FEATURE:
<223> OTHER INFORMATION: Oligonucleotide as PCR primer

<400> SEQUENCE: 12
tttctaggga gtgccaacag g                                      21

<210> SEQ ID NO 13
<211> LENGTH: 22
<212> TYPE: DNA
<213> ORGANISM: Artificial sequence
<220> FEATURE:
<223> OTHER INFORMATION: Oligonucleotide as PCR primer

<400> SEQUENCE: 13
aacctgagct tgaaccatct cc                                     22

<210> SEQ ID NO 14
<211> LENGTH: 32
<212> TYPE: DNA
<213> ORGANISM: Artificial sequence
<220> FEATURE:
<223> OTHER INFORMATION: Oligonucleotide as PCR primer

<400> SEQUENCE: 14
ggcactccct agaaaatcga ttttcgttcg tg                          32

<210> SEQ ID NO 15
<211> LENGTH: 34
<212> TYPE: DNA
<213> ORGANISM: Artificial sequence
<220> FEATURE:
<223> OTHER INFORMATION: Oligonucleotide as PCR primer

<400> SEQUENCE: 15
gttcaagctc aggttcatat gcaagggttt attg                        34

<210> SEQ ID NO 16
<211> LENGTH: 22
<212> TYPE: DNA
<213> ORGANISM: Artificial sequence
<220> FEATURE:

<223> OTHER INFORMATION: Oligonucleotide as PCR primer

<400> SEQUENCE: 16
aacctgagct tgaaccatct cc                                                  22

<210> SEQ ID NO 17
<211> LENGTH: 17
<212> TYPE: DNA
<213> ORGANISM: Artificial sequence
<220> FEATURE:
<223> OTHER INFORMATION: Oligonucleotide as PCR primer

<400> SEQUENCE: 17
atcgattttc gttcgtg                                                        17

<210> SEQ ID NO 18
<211> LENGTH: 37
<212> TYPE: DNA
<213> ORGANISM: Artificial sequence
<220> FEATURE:
<223> OTHER INFORMATION: Oligonucleotide as PCR primer

<400> SEQUENCE: 18
ggcactccct agaaaattat ttcatctcca ttgtccc                                  37

<210> SEQ ID NO 19
<211> LENGTH: 40
<212> TYPE: DNA
<213> ORGANISM: Artificial sequence
<220> FEATURE:
<223> OTHER INFORMATION: Oligonucleotide as PCR primer

<400> SEQUENCE: 19
taggaattat aaccataggt tataattcct tatgtatttg                               40

<210> SEQ ID NO 20
<211> LENGTH: 23
<212> TYPE: DNA
<213> ORGANISM: Artificial sequence
<220> FEATURE:
<223> OTHER INFORMATION: Oligonucleotide as PCR primer

<400> SEQUENCE: 20
atggctacca cctctttagc ttc                                                 23

<210> SEQ ID NO 21
<211> LENGTH: 34
<212> TYPE: DNA
<213> ORGANISM: Artificial sequence
<220> FEATURE:
<223> OTHER INFORMATION: Oligonucleotide as PCR primer

<400> SEQUENCE: 21
gaacgaaaat cgatttacac gcgcggttcg gcgg                                     34

<210> SEQ ID NO 22
<211> LENGTH: 18
<212> TYPE: DNA
<213> ORGANISM: Artificial sequence
<220> FEATURE:
<223> OTHER INFORMATION: Oligonucleotide as PCR primer

<400> SEQUENCE: 22
cgtcgcaggg taatcaac                                                       18

-continued

```
<210> SEQ ID NO 23
<211> LENGTH: 18
<212> TYPE: DNA
<213> ORGANISM: Artificial sequence
<220> FEATURE:
<223> OTHER INFORMATION: Oligonucleotide as PCR primer

<400> SEQUENCE: 23
gtatgaggaa atcaacag                                                   18

<210> SEQ ID NO 24
<211> LENGTH: 132
<212> TYPE: PRT
<213> ORGANISM: Artificial Sequence
<220> FEATURE:
<223> OTHER INFORMATION: GenBank ID ELR88577.1, syn7509DRAFT_00022930

<400> SEQUENCE: 24

Met Asn Lys Lys Lys Val Glu Pro Leu Thr Gly Gln Glu Leu Leu
1               5                   10                  15

Asp Lys Val Lys Glu Leu Glu Ser Ile Ser Lys Glu Gln Lys Ala Lys
            20                  25                  30

Glu Cys Gly Tyr Tyr Thr Ile Thr Lys Asn Gly Val Glu Arg Val Asn
        35                  40                  45

Met Met Lys Phe Leu Asn Ala Leu Ile Asp Ala Glu Gly Ile Glu Leu
    50                  55                  60

Asp Ser His Ser Ser Ser Asp Gly Arg Gly Arg Ser Ala Ser Tyr
65                  70                  75                  80

Lys Ile Ser Val Gln Gln Asn Lys Asn Leu Leu Ile Gly Ser Ala Tyr
                85                  90                  95

Thr Lys Gln Met Gly Leu Glu Pro Gly Asp Glu Phe Lys Ile Thr Leu
            100                 105                 110

Gly Arg Lys His Ile Arg Leu Gln Gln Leu Glu Arg Glu Asp Asp Thr
        115                 120                 125

Glu Ala Thr Ala
    130

<210> SEQ ID NO 25
<211> LENGTH: 629
<212> TYPE: PRT
<213> ORGANISM: Artificial Sequence
<220> FEATURE:
<223> OTHER INFORMATION: GenBank ID ELR87398.1, syn7509DRAFT_00010940

<400> SEQUENCE: 25

Met Leu Asn Thr Pro Ser Lys Arg Thr Ala Asp Tyr Ala Asn Val Gln
1               5                   10                  15

Ser Ile Pro Glu Ile Trp Ala Ile Ala Ile Gln Lys Phe Gly Asp Thr
            20                  25                  30

Val Ala Leu Lys Asp Pro His Val Gln Pro Glu Val Ser Leu Thr Tyr
        35                  40                  45

Ser Gln Leu Tyr Gln Gln Ile Gly Gln Phe Ala Ala Gly Leu Gln Ala
    50                  55                  60

Leu Gly Ile Lys His Gly Asp Arg Ile Ser Leu Phe Ala Glu Asn Gln
65                  70                  75                  80

Pro Arg Trp Leu Val Ala Asp Gln Gly Ile Met Thr Ala Gly Ala Ile
                85                  90                  95

Asn Ala Val Arg Gly Ala Gln Ala Asp Arg Glu Glu Leu Leu Tyr Ile
            100                 105                 110
```

-continued

Leu Ser His Ser Asp Ser Met Ala Leu Val Val Gln Asp Asn Ala Thr
            115                 120                 125

Leu Gln Lys Leu Leu Thr Glu Gly Lys Leu Pro Val Asn Leu Ala Ile
130                 135                 140

Ile Leu Ser Asp Glu Gln Pro Pro Glu Ile Ala Asn Thr Lys Thr Leu
145                 150                 155                 160

Asn Tyr Ser Gly Val Thr Ser Leu Gly Ala Asn His Thr Leu Gln Pro
                165                 170                 175

Val Gln Arg Arg Lys Glu Asp Leu Ala Thr Leu Met Tyr Thr Ser Gly
            180                 185                 190

Thr Ser Gly Gln Pro Lys Gly Val Met Leu Ser Gln Gly Asn Leu Leu
        195                 200                 205

Ser Gln Val Phe Gly Ala Ser Ala Val Val Glu Pro Gln Pro Gly Glu
    210                 215                 220

Val Val Met Ser Ile Leu Pro Ile Trp His Cys Tyr Glu Arg Ser Phe
225                 230                 235                 240

Glu Tyr Phe Ile Leu Ala His Gly Cys Thr Gln Ile Tyr Thr Asn Ile
                245                 250                 255

Arg Tyr Val Lys Lys Asp Phe Lys Glu Phe Lys Pro Phe Tyr Met Val
            260                 265                 270

Gly Val Pro Arg Leu Trp Glu Ser Ile Tyr Glu Gly Val Gln Lys Gln
        275                 280                 285

Phe Arg Glu Gln Ser Ala Asn Lys Gln Lys Leu Ile Asn Phe Phe Phe
    290                 295                 300

Ala Gln Ser Gln Arg Tyr Ile Met Ala Arg Arg Val Val Gln Gly Leu
305                 310                 315                 320

Asp Leu Asn Asn Leu Tyr Pro Ser Ser Leu Ala Lys Leu Trp Ala Arg
                325                 330                 335

Ile Gln Ile Ile Pro Leu Gly Leu Ile His Gln Leu Ala Asp Lys Ile
            340                 345                 350

Ile Tyr Lys Gln Val Arg Glu Ala Thr Gly Gly Lys Val Lys Phe Leu
        355                 360                 365

Val Ser Gly Gly Gly Ser Ile Ala Glu His Leu Glu Asp Phe Tyr Glu
    370                 375                 380

Ile Val Gly Val Asp Ile Leu Gly Gly Tyr Gly Leu Thr Glu Thr Ser
385                 390                 395                 400

Pro Ile Thr His Val Arg Arg Thr Trp Arg Asn Leu Arg Gly Ala Asp
                405                 410                 415

Gly Gln Pro Leu Pro Asp Thr Glu Thr Gln Ile Val Glu Leu Glu Ser
            420                 425                 430

His Lys Pro Leu Pro Val Gly Lys Lys Gly Leu Val Met Ile Arg Gly
        435                 440                 445

Ser Gln Val Met Gln Gly Tyr Tyr Lys Asn Pro Glu Ala Thr Ala Lys
    450                 455                 460

Ala Ile Asn Ser Glu Gly Trp Phe Asn Thr Gly Asp Leu Gly Trp Val
465                 470                 475                 480

Ser Lys Gln Asn Asp Leu Val Ile Thr Gly Arg Ala Lys Asp Thr Ile
                485                 490                 495

Val Leu Ser Asn Gly Glu Asn Ile Glu Pro Gln Pro Ile Glu Asn Ala
            500                 505                 510

Cys Leu Arg Ser Pro Tyr Ile Asp Gln Ile Met Leu Val Gly Gln Asp
        515                 520                 525

Glu Arg Ser Leu Gly Ala Leu Ile Val Pro Asn Gln Asp Ala Leu Gln

```
                530                 535                 540

Gln Trp Ala Thr Thr Gln Asn Pro Ala Ile Asp Pro Ser Asn Leu Gly
545                 550                 555                 560

Asn Lys Ala Ile Leu Asp Leu Tyr Arg Leu Glu Val Ser Arg Glu Val
                565                 570                 575

Gln Asn Arg Pro Gly Tyr Arg Pro Asp Glu Arg Ile Ser Thr Phe Lys
            580                 585                 590

Leu Ile Ala Glu Pro Phe Ser Ile Glu Asn Gly Thr Met Thr Gln Thr
        595                 600                 605

Leu Lys Ile Lys Arg Ser Val Val Met Asp Arg Tyr His Asp Ile Ile
    610                 615                 620

Asp Lys Met Phe Ala
625
```